United States Patent
Hanko et al.

(10) Patent No.: US 9,201,039 B2
(45) Date of Patent: Dec. 1, 2015

(54) MEASURING TRANSDUCER FOR DETERMINING A MEASURED VARIABLE REPRESENTING A CONTENT OF $H^+$ AND/OR $OH^-$ IONS IN A MEASURED MEDIUM

(75) Inventors: Michael Hanko, Dresden (DE); Thomas Wilhelm, Halle (DE); Manfred Jagiella, Nürtingen-Reudern (DE)

(73) Assignee: Endress + Hauser Conducta Gesellschaft für Mess- und Regeltechnik mbH + Co. KG, Dieselstr., Gerlingen (DE)

( * ) Notice: Subject to any disclaimer, the term of this patent is extended or adjusted under 35 U.S.C. 154(b) by 358 days.

(21) Appl. No.: 13/530,459

(22) Filed: Jun. 22, 2012

(65) Prior Publication Data
US 2012/0325659 A1 Dec. 27, 2012

(30) Foreign Application Priority Data
Jun. 24, 2011 (DE) .......................... 10 2011 078 059

(51) Int. Cl.
| | |
|---|---|
| *G01N 27/333* | (2006.01) |
| *G01N 27/30* | (2006.01) |
| *G01N 21/80* | (2006.01) |
| *G01N 27/414* | (2006.01) |

(52) U.S. Cl.
CPC ............ *G01N 27/3335* (2013.01); *G01N 21/80* (2013.01); *G01N 27/302* (2013.01); *G01N 27/414* (2013.01)

(58) Field of Classification Search
CPC ... G01N 27/301; G01N 27/302; G01N 27/32; G01N 27/36; G01N 27/333–27/401; G01N 27/414–27/4148; G01N 27/4035; G01N 21/80
See application file for complete search history.

(56) References Cited

U.S. PATENT DOCUMENTS

| | | | | |
|---|---|---|---|---|
| 5,061,976 | A * | 10/1991 | Shimomura et al. | 257/414 |
| 5,133,856 | A * | 7/1992 | Yamaguchi et al. | 204/416 |
| 5,607,644 | A * | 3/1997 | Olstein et al. | 422/82.07 |
| 2002/0093008 | A1 * | 7/2002 | Kerres et al. | 252/500 |

(Continued)

FOREIGN PATENT DOCUMENTS

| | | |
|---|---|---|
| DE | 69612624 T2 | 9/2001 |
| DE | 102008055107 A1 | 7/2010 |
| WO | 2007/082350 A1 | 7/2007 |

OTHER PUBLICATIONS

Choi et al. "Thermodynamics and Proton Transport in Nafion-II. Proton Diffusion Mechanisms and Conductivity," Journal of the Electrochemical Society, 152(3), E123-E130 (2005) (Worcester Polytechnic Institute, Chemical Engineering Faculty Publications, Jan. 1, 2005).*

(Continued)

*Primary Examiner* — Alexander Noguerola
(74) *Attorney, Agent, or Firm* — Bacon & Thomas, PLLC (57) ABSTRACT

A measuring transducer, which is embodied to produce and output a measurement signal dependent on the content of $H^+$ and/or $OH^-$ ions present in a measured medium, wherein the measuring transducer has, in a region provided for contact with the measured medium, at least one polymer membrane selectively conducting $H^+$ and/or $OH^-$ ions. The polymer membrane can comprise an $H^+$ ion conducting polymer and/or an $OH^-$ ion conducting polymer.

14 Claims, 5 Drawing Sheets

(56) References Cited

U.S. PATENT DOCUMENTS

| | | | |
|---|---|---|---|
| 2005/0016847 A1* | 1/2005 | Buehler | 204/412 |
| 2010/0032661 A1* | 2/2010 | Osterbacka et al. | 257/40 |
| 2011/0248731 A1* | 10/2011 | Sastry et al. | 324/693 |

OTHER PUBLICATIONS

Kim et al., "Anhydrous Proton-Conducting Properties of Nafion-1,2,4-Triazole and Nafion-Benzimidazole Membranes for Polymer Electrolyte Fuel Cells," Journal of the Electrochemical Society, 154 (4) A290-A294 (2007).*

German Search Report in corresponding German Application No. 10 2011 078 059.9, dated Apr. 23, 2012.

Buhlmann et al., "Carrier-Based Ion-Selective Electrodes and Bulk Optodes. 2. Ionophores for Potentiometric and Optical Sensors", Chem. Rev., 1998, vol. 98, pp. 1593-1687.

* cited by examiner

MEASURING TRANSDUCER FOR DETERMINING A MEASURED VARIABLE REPRESENTING A CONTENT OF H⁺ AND/OR OH⁻ IONS IN A MEASURED MEDIUM

TECHNICAL FIELD

The invention relates to a measuring transducer for determining a measured variable representing a content of $H^+$ and/or $OH^-$ ions in a measured medium, especially an activity and/or a concentration of $H^+$ ions and/or $OH^-$ ions.

BACKGROUND DISCUSSION

The content of $H^+$ or $H_3O^+$ ions in a measured medium, especially the activity and/or concentration of these ions in the measured medium, is an important measured variable in environmental analytics as well as in a number of chemical or biochemical processes in the laboratory or in industrial processes. The $H^+$ ion content of a measured medium, as a rule, is given as a dimensionless pH value, which is formed by the negative base 10 logarithm of the $H^+$ ion activity in the measured medium. To a first approximation, in dilute solutions, the $H^+$ ion activity can be set to equal the $H^+$ ion concentration. Analogously to the pH value, the pOH value is defined as the negative base 10 logarithm of the $OH^-$ ion activity, or, to a good approximation, of the $OH^-$ ion concentration in dilute solutions. The two values are related to one other through the constant ionic product of water $$pH + pOH = 14.$$

From the pH value or the pOH value, thus, the associated $H^+$ ion or $OH^-$ ion activities and/or the corresponding concentrations can be correspondingly ascertained.

The most popular technology for determining the pH value of a measured solution is potentiometric measurement. A single rod, measuring chain frequently referred to as a glass electrode serves most frequently as a measuring transducer for the potentiometric measurement of the pH value; the single rod, measuring chain combines a pH sensitive, measuring half cell and a reference half cell, which provides a stable reference potential, which is independent of the pH value of the measured medium. The measuring half cell comprises, as a rule, a tubular glass housing closed on one end by a membrane comprising a pH sensitive glass; the tubular glass housing is filled with an internal electrolyte, for example, a buffer solution containing chloride; a potential sensing element, for example, a chloridized silver wire, extends into the buffer solution. In contact with the measured medium, a measuring half cell potential dependent on the pH value forms at the glass membrane. Serving, as a rule, as reference half cell is a reference electrode of second type, for example, an Ag/AgCl or calomel electrode. The potential difference between the measuring half cell potential tappable at the potential sensing element of the measuring half cell and the reference potential (which is ideally independent of the pH value of the measured medium) of the reference half cell forms the primary signal of the measuring transducer and is a direct measure for the pH value of the measured medium.

Although such potentiometric measuring transducers assure very precise and reliable measurement results and are well established both in the laboratory as well as in process analytics, they have a number of disadvantages. Especially the very thin, pH sensitive, glass membrane is very difficult to manufacture and is extraordinarily sensitive to handling.

Breaking the glass membrane can lead to glass shards getting into the measured medium. If the measured medium is, for example, a product, or an intermediate product, manufactured in a pharmaceutical or food process, the measured medium must be discarded upon such a glass fracture, in order to avoid endangering the end consumer by glass shards in the product.

Due to the small conductivity of the pH sensitive glass membrane, it is additionally necessary to measure the potential difference between the leads of the measuring transducer with very high impedance, which can lead to instabilities in the measuring and corruptions of the measured value. Due to the high resistance of the glass that forms the glass membrane, miniaturization of the pH glass electrode is limited, since the resistance of the measuring half cell continually rises with the reduction of the area of the glass membrane. There has long been the need for alternative measuring methods using more robust measuring transducers for determining the pH or pOH value.

Recently, above all, measuring of the pH value by means of an ion selective, field effect transistor (ISFET) and optical pH measurement have achieved a certain importance.

An ISFET measuring transducer includes an ISFET semiconductor chip, which basically corresponds to a MOSFET in its construction, wherein the metal gate, in the case of the ISFET, is replaced by an ion selective layer, for example, an $H^+$ ion selective layer. Such an ISFET has a semiconducting substrate, for example, an n-conducting substrate, in which two p-conducting areas, which function as the source and the drain of the ISFET, are embedded. The area between the source and the drain serves as a semiconductor channel, which is isolated from the ion selective layer by an insulation layer. If the ion selective layer is impacted by the measured medium, its pH value influences the number of charge carriers in the semiconductor channel between the source connection and the drain connection. ISFETs can thus be considered electronic components, whose threshold voltage can be changed by the surface potential formed at the oxide, measured liquid interface by the contacting of the pH sensitive coating with the measured medium. By exploiting this effect, a measurement circuit of an ISFET measuring transducer produces an electrical output signal, which is correlated with the pH value of the measured liquid. A pH measuring device having a measuring transducer comprising an ISFET is described, for example, in DE 19857953 C2.

The mechanical stability of an ISFET measuring transducer is, indeed, greater than that of a glass electrode; however, the known pH sensitive, metal oxide layers are sensitive to aggressive measured media, for example, strongly alkaline measured media, especially at increased temperatures. Additionally, ISFET measuring transducers cannot be sterilized by irradiating with beta or gamma radiation, as is common, for example, in medicinal or biotechnological applications.

Measuring transducers for optical pH measurements comprise a pH indicator immobilized in a sensor matrix; the pH indicator's optical properties, for example, its absorption spectrum or fluorescence spectrum, are influenced by the pH value of the measured medium contacting the indicator. Frequently, a polymer membrane or a porous solid structure serves as the sensor matrix. Measuring transducers for optical pH measuring further comprise an optical measuring arrangement for registering the influenced optical property. The optical measuring arrangement is suitably embodied, depending on the type of indicator and the optical property influenced by the pH value. If the influenced optical property is, for example, the intensity of a fluorescent emission by the indicator at a fixed wavelength, the optical measuring arrangement can have, for example, one or more radiation sources for initiating the fluorescence, and one or more photoelectric elements for registering the fluorescent radiation at, in given cases, a fluorescence wavelength. The photocurrent output by the photoelectric element or an electrical signal derived therefrom forms the measurement signal of the optical pH measuring transducer. Such measuring transducers are described, for example, in DE 10 2008 033214 A1. Optical measuring transducers for pH measurement are robust and relatively inexpensive to manufacture. However, many additional factors, especially cross sensitivities to other ions present in the measured medium, influence the immobilized indicator and so corrupt the measurement result.

SUMMARY OF THE INVENTION

It is, in view of this state of the art, an object of the invention to provide a measuring transducer for determining a measured variable representing the content of $H^+$ ions or $OH^-$ ions in a measured medium, especially a pH value or a pOH value, which measuring transducer is easier to miniaturize compared to the measuring transducers known from the state of the art and has an improved mechanical and/or chemical stability and possesses, also, a high selectivity.

This object is achieved by a measuring transducer, which is embodied to produce and output a measurement signal dependent on the content of $H^+$ and/or $OH^-$ ions present in the measured medium, wherein the measuring transducer has, in a region provided for contact with the measured medium, at least one polymer membrane selectively conducting $H^+$ and/or $OH^-$ ions.

A polymer membrane selectively conducting $H^+$ ions or protons is a polymer membrane, whose conductivity or permeability to protons is higher than its conductivity or permeability to other ions present in the measured medium, especially cations such as alkali or ammonium ions, by a factor of at least 10, preferably at least 100, especially preferably at least 1000. A polymer membrane selectively conducting hydroxide ions is a polymer membrane, whose conductivity or permeability to hydroxide ions is higher than its conductivity or permeability to other ions present in the measured medium, especially anions such as halogen ions, by a factor of at least 10, preferably at least 100, especially preferably at least 1000.

The polymer membrane selectively conducting $H^+$ and/or $OH^-$ ions can comprise, for example, an $H^+$ ion and/or an $OH^-$ ion conducting polymer. For example, the polymer membrane can be an $H^+$ ion conducting polymer. In this case, the polymer membrane selectively conducts protons. In another example of an embodiment, the polymer membrane can be an $OH^-$ ion conducting polymer. In this other example of an embodiment the polymer membrane selectively conducts $OH^-$ ions.

Proton conducting and hydroxide conducting polymers are especially investigated in connection with the development of fuel cells. For example, the firm, Tokuyama Corporation, Shibyu, Shibuya-ku, Tokyo, Japan offers both selectively as well as selectively $OH^-$, conductive, polymer membranes for use in fuel cells, as shown in the prospectuses "DMFC Membrane and Ionomer Solution," Tokuyama Corporation, February 2011, and "Anion Conductive Membrane and Ionomer Solution," Tokuyama Corporation, February 2011.

Also many publications deal with proton conducting polymers, especially for use in fuel cells. For example, the article by X.-G. Sun, at al.: "New polymeric proton conductors for water-free and high temperature fuel cells," *Prepr. Pap.-Am. Chem. Soc., Div. Fuel Chem*, 2004, 49(2), 596 describes proton conductors, which have a backbone, to which are bonded, by means of flexible side chains, groups serving as proton solvents, for example, imidazole groups and acid groups, for example, fluoroalkyl sulfonyl imide groups. Such a structure is said to be able to conduct protons by means of structural diffusion.

The dissertation of G. E. Scharfenberger, "Wasserfreie, polymere Protonenleiter für Brenstoffzellen durch Immobilisierung von Imidazol," [Anhydrous Polymeric Proton Conductors for Fuel Cells by Immobilizing Imidazole], Johannes Gutenberg University, Mainz, 2003, describes investigations of the proton conductivity of comb-like polysiloxane having imidazole covalently bonded to the side chains of the polysiloxane and serving as proton solvent. These investigations show that the $H^-$ ion conduction in these materials occurs anhydrously by means of structural diffusion. The possibility of influencing the proton conductivity by doping is also described in this work.

The dissertation of S. Hinz, "Wasserfreie Protonenleiter für Brennstoffzellen auf der Basis von Imidazol and Benzimidazol: Synthese and Charakterisierung," [Anhydrous Proton Conductor for Fuel Cells Based on Imidazole and Benzimidazole: Synthesis and Characterization] Johannes-Gutenberg-Universität, Mainz, 2005, describes investigations of proton conduction based on imidazole and benzimidazole for use as a material for proton conducting membranes in anhydrous PEM fuel cells. The investigations concern polythiophene having side chains containing imidazole or benzimidazole, wherein the thermal characteristics and conductivity of the material, doped in given cases with $H_3PO_4$, were studied.

DE 10 2004 023 586 A1 describes a proton conductive, cross linked heteropolysiloxane having a polysiloxane basic structure, comprising sulfonic acid groups and/or carboxyl groups, which, in each case, are bound to particular Si atoms of the polysiloxane basic structure via an organic spacer, as well as either nitrogen containing aromatic heterocyclics in the ring, which, in each case, are bound to particular Si atoms of the polysiloxane basic structure via an organic spacer comprising an amide functional group, or nitrogen containing aromatic heterocyclics in the ring, which, in each case, are bound to Si atoms of the polysiloxane basic structure via an organic spacer. Proton conductive membranes comprising these materials are said to be distinguished by a high proton conductivity, very good chemical resistance, low gas permeability and high temperature stability.

This and other proton or hydroxide ion conducting polymers can serve as a material for the selectively proton and/or hydroxide ion conducting, polymer membrane of a measuring transducer of the invention.

Polymer membranes are more mechanically stable than the $H^+$ selective glass membrane of known potentiometric pH glass electrodes. Consequently, they can be applied advantageously in a potentiometric measuring transducer for pH measuring, for example, instead of the glass membrane of a pH glass electrode, whereby the danger of mechanical damage to the measuring transducer in measurement operation or in handling of the measuring transducer is significantly reduced.

In this embodiment the selectively proton and/or hydroxide ion conducting, polymer membrane serves as the sensitive element of the measuring transducer. During measurements, when the polymer membrane is immersed in the measured medium, a potential which depends on the activity of protons and/or hydroxide ions in the measured medium forms at the polymer membrane, in as similar way as in the case of a glass membrane in a known glass electrode.

Polymer membranes often have a higher ion conductivity than the established glass membranes used in pH glass electrodes. This means that the potential output by the measuring transducer can be measured at less high impedance, which affects the stability of the measurement signal and the disturbance sensitivity positively. Also, a miniaturization of the potentiometric measuring transducer is facilitated by the higher conductivity of the polymer membranes in comparison to pH selective glass membranes. In optical measuring transducers, the selectively proton and/or hydroxide ion conducting, polymer membrane can spatially separate a sensitive element of the measuring transducer, for example, a sensor matrix, in which a pH indicator is immobilized, from the measured medium, so that only $H^+$ and/or or $OH^-$ ions reach the sensor matrix through the membrane. This leads to an increase in the selectivity and stability of the optical measuring transducer. Similarly, a selectively proton and/or hydroxide ion conducting, polymer membrane can spatially separate the gate of a FET measuring transducer from the measured medium and so likewise serve to increase the selectivity and stability of the measuring transducer, as is explained below.

The measuring transducer can be connected to an evaluation circuit. The evaluation circuit can be embodied to receive the measurement signal from the measuring transducer and to output the measurement signal to a superordinated unit, for example, a measurement transmitter, a programmable logic controller, a computer, a process control system or other data processing work. The evaluation circuit can especially be embodied to process the measurement signal received from the measuring transducer, before the measurement signal is output to the superordinated unit. For example, the evaluation circuit can amplify the measurement signal and/or convert it from an analog signal into a digital signal. The evaluation circuit can be correspondingly adapted to the type of charge carriers transported through the polymer membrane, namely $H^+$ or $OH^-$.

Preferably, a proton conducting and/or hydroxide ion conducting polymer forming the polymer membrane conducts protons or hydroxide ions intrinsically, i.e. by means of structural diffusion, especially by means of a Grotthuss type mechanism through the transfer of protons or hydroxide ions between functional groups arranged in spatial proximity to one another, especially neighboring one another. The functional groups participating in the conduction of protons or hydroxide ions are also referred to as proton solvents or hydroxide ion solvents. One such conduction mechanism for the conduction of $H^+$ in water is known as the Grotthuss mechanism. Conduction by means of structural diffusion assures an especially high selectivity of the measuring transducer.

In an embodiment, in which the polymer membrane is selectively proton conductive, the polymer membrane includes a water free, proton conducting polymer, which has a basic polymer structure, to which groups serving as proton solvents are bound via side chains, especially flexible side chains, which comprise, for example, at least one amide functional group and/or at least one ether group. The groups serving as proton solvents can comprise, for example, aromatic heterocyclics, especially imidazoles, benzimidazoles or pyrazoles.

In this embodiment, acid groups can be supplementally bonded to the basic polymer structure via side chains, especially flexible side chains. The additional acid groups provide movable protons for proton conduction; they serve, thus, as the doping of the conductive polymer. The acid groups can comprise, for example, sulfonic acid groups and/or carboxyl groups.

The measuring transducer can be embodied as a potentiometric pH sensor. This pH sensor can comprise a measuring half cell and a reference half cell. The measuring half cell, for example, can have a housing, which surrounds a measuring half cell space containing a buffered, preferably a pH buffered and chloride ion containing, inner electrolyte solution and which is sealed by a proton or hydroxide conductive polymer membrane, especially a selectively proton or hydroxide conductive polymer membrane, in a region specifically for contact with the measured medium. A potential sensing element of the measuring half cell, for example, a silver wire, preferably a chloridized silver wire, can extend into the buffer solution. The reference half cell can have a conventional reference electrode of second type, for example, an Ag/AgCl electrode or an $Hg/Hg_2Cl_2$ electrode. For example, the reference half cell can have a housing, in which a reference half cell space containing a reference electrolyte solution, e.g. an aqueous KCl solution, is formed; the reference half cell space is in contact with a medium surrounding the pH probe, for example, the measured medium, in the measurement operation of the measuring probe, for charge equalization via, for example, a liquid junction formed by a diaphragm. A potential sensing element of the reference half cell, formed, for example, by a chlorided silver wire, is immersed in the reference electrolyte solution. The potential difference tappable on the potential sensing elements serves as a measurement signal of the measuring transducer. For example, the potentiometric pH sensor can be embodied as a single rod, measuring chain.

In a further embodiment, the selectively proton and/or hydroxide ion conducting, polymer membrane can spatially separate a sensitive element of the measuring transducer from the measured medium. Due to the proton or hydroxide ion conductivity of the polymer forming the polymer membrane, $H^+$ or $OH^-$ ions can be led through the polymer membrane to the sensitive element, so that of all ions present in the measured medium and other components of the measured medium, only $H^+$ or $OH^-$ ions come in contact with the sensitive element. This leads to an increase in the selectivity of the measuring transducer. At the same time, the polymer membrane protects the sensitive element from mechanical or chemical loadings.

A sensitive element of the measuring transducer is an element, for example, a surface, a polymer membrane or a circuit, which, in interaction with the measured medium, is embodied to influence the measurement signal of the measuring transducer as a function of the measured variable. In an optical measuring transducer for measuring an $H^+$ or $OH^-$ content of the measured medium, the sensitive element can be, for example, a sensor matrix, which contains a pH sensitive indicator. In a FET measuring transducer for measuring an $H^+$ or $OH^-$ content of the measured medium, the sensitive element can be a field effect transistor assembly, especially a field effect transistor having an insulated gate, preferably a MISFET (Metal Insulator Semiconductor Field Effect Transistor), a MOSFET (Metal Oxide Semiconductor Field Effect Transistor) or an ISFET (Ion Sensitive Field Effect Transistor). For example, the gate of the FET measuring transducer can be spatially separated from the measured medium by the polymer membrane comprising a proton and/or hydroxide ion conducting polymer.

It is also possible to use the polymer membrane selectively conducting $H^+$ and/or $OH^-$ ions for increasing the selectivity of a measuring transducer comprising a metal oxide electrode, also commonly referred to as metal electrode or metal/metal oxide electrode. For example, the measuring transducer can be a potentiometric measuring transducer comprising a common reference half cell and a metal oxide electrode as its measuring half cell. A typical example of a metal oxide electrode is the antimony electrode, which comprises antimony metal covered by a thin layer of antimony (III) oxide $Sb_2O_3$. The potential of the metal oxide electrode or metal electrode, respectively, is not only dependent on the pH value of the measured medium, but it is likewise influenced by any other redox system present in the measured medium. By separating the sensitive region of the metal oxide electrode from the measured media by the polymer membrane selectively conducting $H^+$ and/or $OH^-$ ions, the selectivity of the measuring transducer for pH measurements can be increased. The antimony electrode is responsive to the activity of $OH^-$ ions in the measured media. Hence, it is advantageous to use a polymer membrane selectively conducting $OH^-$ ions for separating the antimony oxide layer from the measured medium, when an antimony oxide electrode is used as the measurement half cell in this embodiment.

In an embodiment, this spatial separation can be realized by providing the selectively proton or hydroxide ion conducting polymer membrane, for example, as a coating covering the gate of an ISFET measuring transducer or as a separation membrane spatially separating the gate from the measured medium. This leads not only to an improvement of the selectivity of the ISFET measuring transducer, but, also, serves as protection from chemical attack on the gate coating, especially at high temperatures and high pH values, and, thus, increases the stability of the measuring transducer.

In an additional embodiment of a MISFET or MOSFET measuring transducer, the metal layer of the gate can be connected to a solid metal potential sensing element, which is brought into contact with the measured medium for performing a measuring of the $H^+$ or $OH^-$ content. The area of the solid potential sensing element provided for contact with the measured medium is coated with a proton or hydroxide conducting polymer in this embodiment, so that the polymer forms a polymer membrane, which spatially separates the solid potential sensing element from the measured medium. In this way, it is assured that the measuring transducer has a high selectivity.

The selectively proton or hydroxide ion conducting, polymer membrane can likewise be used for increasing the selectivity of an optical measuring transducer for determining a measured variable representing a concentration of $H^+$ and/or $OH^-$ ions in a measured medium. The optical measuring transducer can have in an area established for immersion in the measured medium a sensor matrix, e.g. a polymer membrane or a porous solid body; the sensor matrix comprises an immobilized pH or pOH sensitive indicator and is spatially separated from the measured medium by the proton or hydroxide ion conducting, polymer membrane. At the same time, the proton or hydroxide ion conducting, polymer membrane serving as separating diaphragm protects the measuring transducer against washing out of the indicator from the sensor matrix and, thus, increases the stability of the measuring transducer.

A measuring arrangement can include at least one measuring transducer according to one of the embodiments described above. The measuring arrangement can furthermore have a measurement circuit, or can be connectable to a measurement circuit, embodied to receive a measurement signal issued by the at least one measuring transducer, in given cases, for processing and outputting the measurement signal to a superordinated unit, e.g. a computer, a measurement transmitter, a programmable logic controller or a process control station, and/or to a user interface, e.g. a display. The processing of the measurement signal of the measuring transducer can comprise, for example, amplification, smoothing, integration or converting an analog signal into a digital signal.

BRIEF DESCRIPTION OF THE DRAWINGS

The invention will now be described in greater detail in the following based on the examples of embodiments shown in the drawing, the figures of which show as follows.

DETAILED DISCUSSION IN CONJUNCTION WITH THE DRAWINGS

Figure 1:
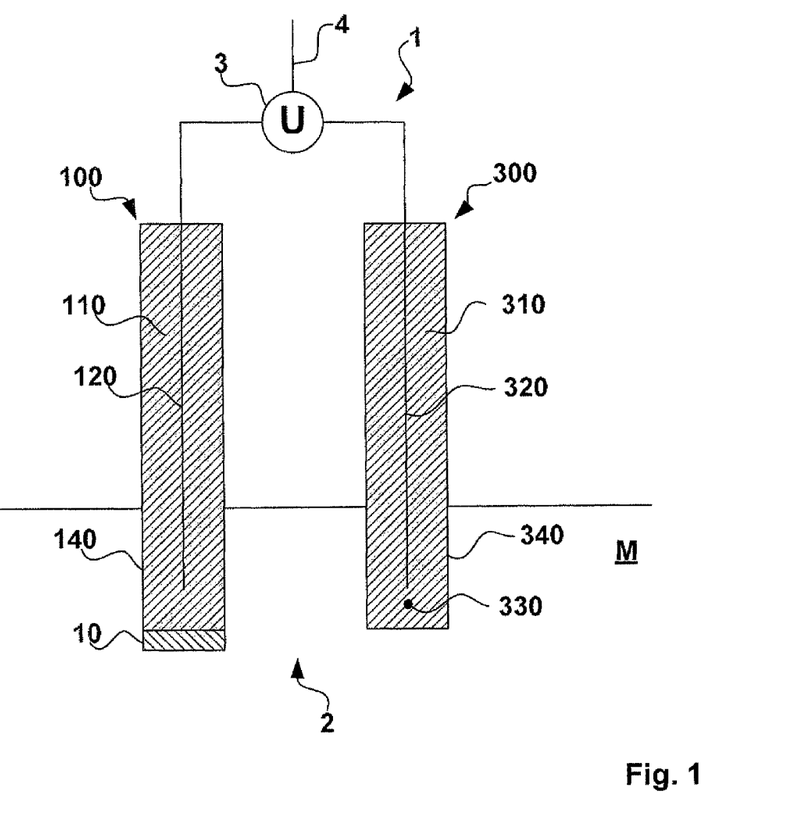
FIG. 1 is a potentiometric measuring transducer, which has a selectively proton conducting, polymer membrane, for determining a measured variable representing $H^+$ or $OH^-$ content in a measured medium.

FIG. 1 shows schematically a measuring arrangement 1 having a potentiometric measuring transducer 2 for determining a measured variable representing $H^+$ or $OH^-$ content in a measured medium, for example, a pH value. Measuring transducer 1 includes a measuring half cell 100 and a reference half cell 300. Measuring half cell 100 includes a housing 140, which contains an internal electrolyte 110, for example, a buffer solution containing chloride; the front end of housing 140 specifically for immersion in measured medium M is sealed by a polymer membrane 10. Polymer membrane 10 is, in the example shown here, selectively proton conducting. For this, polymer membrane 10 can be a selectively proton conducting polymer of the type described above. When the proton conducting, polymer membrane 10 is immersed in a measured medium, a potential dependent on the difference of the pH values in the buffered inner electrolyte solution 110 and the measured medium M arises on the polymer membrane in a manner analogous to the glass electrodes known for pH measuring. Immersed in inner electrolyte 110 is a first potential sensing element 120, which can be, for example, a chlorided silver wire, and serves to sense the potential arising at the polymer membrane 10.

Reference half cell 300 includes a housing 340, which contains a reference electrolyte 310, into which a second potential sensing element 320 extends, which serves to provide a stable reference potential derived from the reference half cell 300 and essentially independent of the composition of the measured medium. An aqueous halogen salt solution, for example, a KCl solution, can serve as reference electrolyte 310. A chlorided silver wire can serve as potential sensing element 320, so that an Ag/AgCl reference system is formed. Provided in the housing wall of housing 340 is a liquid junction 330, via which reference electrolyte 310 is in contact with a medium surrounding reference half cell 330 for charge equalization. In measurement operation, the housing section surrounding liquid junction 330 is immersed in measured medium M. For example, a passageway or a diaphragm can serve as liquid junction 330.

In the schematic representation of FIG. 1, measuring half cell 100 and reference half cell 300 are accommodated in two housings 140, 340 spatially separated from one another. It is, however, equally possible to embody measuring transducer 2 as a single rod, measuring chain, which has a housing having two chambers fixedly connected with one another, wherein measuring half cell 100 is formed in one chamber and the reference half cell is formed in the other chamber.

The potential difference between potential sensing element 120 of measuring half cell 100 and potential sensing element 320 of reference half cell 300 serves as the measurement signal of measuring transducer 2 dependent on the pH value of measured medium M. First potential sensing element 120 of measuring half cell 100 and second potential sensing element 320 of reference half cell 300 are connected to a measurement circuit for registering, processing and forwarding the measurement signal. Measurement circuit 3 can be accommodated in the housing of measuring transducer 2. However, measurement circuit 3 can also be at least partially be arranged remotely from measuring transducer 2. Measurement circuit 3 can serve for forming a processed signal representing the potential difference between first potential sensing element 120 and second potential sensing element 320. This signal can directly comprise a voltage formed from the potential difference or be a signal derived from the potential difference, especially a signal reinforced, digitized or transformed in some other manner. Measurement circuit 3 is connected via a signal output 4 to a superordinated unit (not shown), especially a measurement transmitter, a bus coupler, a programmable logic controller, a personal computer or a process control system. Using the signal output 4, measurement circuit 3 can output the processed signal to the superordinated unit.

Figure 2:
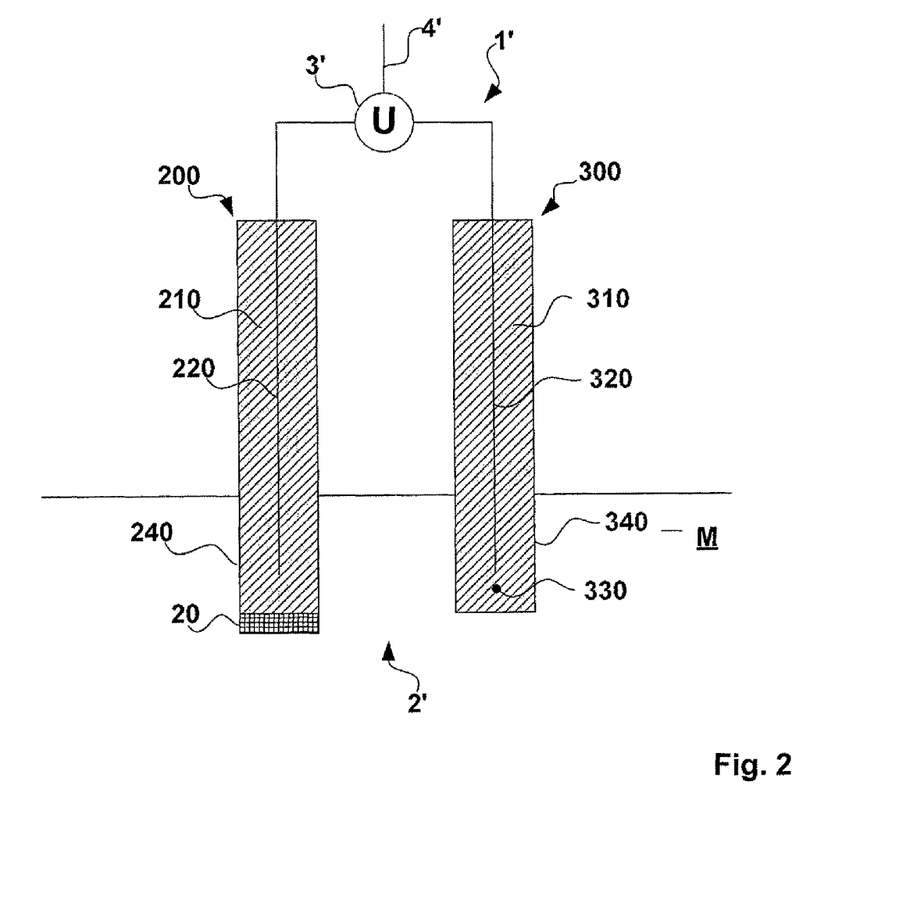
FIG. 2 is a potentiometric measuring transducer, which has a selectively hydroxide ion conducting, polymer membrane, for determining a measured variable representing an $H^+$ or $OH^-$ content in a measured medium.

FIG. 2 shows, schematically, a measuring arrangement 1' having a potentiometric measuring transducer 2', which serves for determining a measured variable representing $OH^-$ concentration in a measured medium, for example, a pOH value. Measuring transducer 2' is basically constructed in the same manner as measuring transducer 2 described in FIG. 1.

Measuring transducer 2' includes a measuring half cell 200 and a reference half cell 300. Measuring half cell 200 includes a housing 240 containing an inner electrolyte; the end region of housing 240 intended for immersion in measured medium M is sealed by a selectively hydroxide ion conducting, polymer membrane 20. A potential sensing element 220, which can, for example, be embodied as a chloridized silver wire, is immersed in the inner electrolyte. Reference half cell 300 is embodied identically to the reference half cell of measuring transducer of FIG. 1. Reference half cell 300 serves to provide a stable reference potential, which is independent of the $H^+$ or $OH^-$ concentration in the measured medium.

Selectively hydroxide ion conducting, polymer membrane 20 comprises a hydroxide ion conducting polymer. As a consequence of the difference between the pOH value of the measured medium and that of the inner electrolyte 210, there arises, between the potential sensing element 220 of the measuring half cell and the potential sensing element 320 of the reference half cell, a potential difference, which serves for measuring transducer 2' as measurement signal representing the pOH value of measured medium M. The measurement circuit 3' registers the potential difference between the potential sensing elements 220 and 320 of the measuring half cell and reference half cell; the potential difference is a measure for the pOH value of the measured medium. As with measurement circuit 3 of measuring transducer 2 of FIG. 1, measurement circuit 3' can at least partially be arranged as a component of measuring transducer 2' or it can be arranged separately therefrom. The measurement signal or a signal derived therefrom is output by measurement circuit 3' via the signal output 4', for example, to a superordinated unit (not shown).

As with measuring transducer 2 of FIG. 1, measuring transducer 2' schematically shown in FIG. 2 can also be embodied as a single rod, measuring chain.

Figure 3:
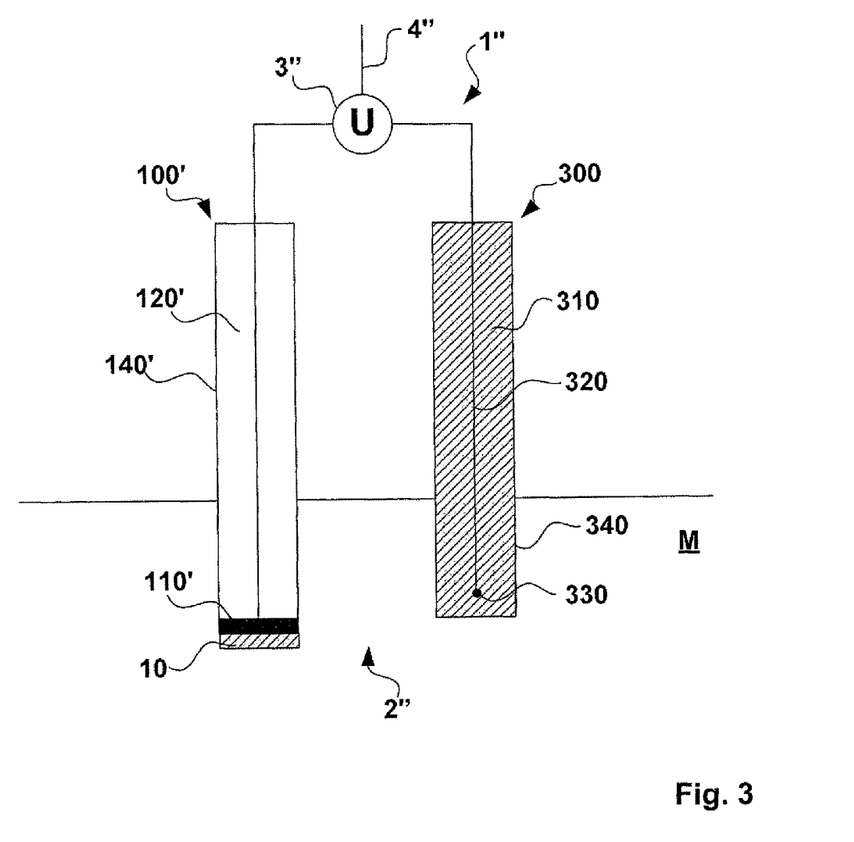
FIG. 3 is a potentiometric measuring transducer, which has a selectively proton conducting, polymer membrane and a solid potential sensing element for sensing the potential arising on the polymer membrane and/or the surface of the solid potential sensing element, for determining a measured variable representing an $H^+$ or $OH^-$ content in a measured medium.

FIG. 3 shows schematically a measuring arrangement 1" having a potentiometric measuring transducer 2" for determining a measured variable representing $H^+$ or $OH^-$ content in a measured medium M. Measuring transducer 2" includes a reference half cell 300, which in the example shown here is identical to reference half cell 300 of measuring transducer 2 or 2' shown in FIG. 1 or 2.

The measuring half cell 100' of measuring transducer 2" includes a selectively proton conducting, polymer membrane 10 in a region intended for immersion in the measured medium. Polymer membrane 10 comprises a proton conducting polymer. Instead of a potential sensing element in contact with the polymer membrane 10 and extending into inner electrolyte, as in the case of measuring half cell 100 of FIG. 1, measuring half cell 100' includes a solid potential sensing element 110'. Solid potential sensing element 110' can be formed, for example, by a platinum layer or platinum disk electrically contacting the polymer membrane; the platinum layer or platinum disk is electrically conductively connected via a platinum wire 120' to measurement circuit 3". Measurement circuit 3" is additionally connected to the potential sensing element 320 extending into reference electrolyte 310 of reference half cell 300 and embodied to form, and, in given cases, to further process, the potential difference between solid potential sensing element 110' and potential sensing element 320 of reference half cell 300, which potential difference serves as a measurement signal of measuring transducer 2". The potential difference or a signal derived therefrom is output by measurement circuit 3" via the signal output 4" of measurement circuit 3" to a superordinated unit (not shown). The potential difference is a direct measure for the pH value of measured medium M.

Alternatively, the measuring transducer can also have a selectively hydroxide ion conducting, polymer membrane instead of selectively proton conducting, polymer membrane 10 and otherwise be identically constructed as the example in FIG. 3. In this case, the potential difference between the solid potential sensing element of the measuring half cell and the potential sensing element of the reference half cell is a direct measure for the pOH value of the measured medium. As explained above, there is a direct relationship between the pH value and the pOH value of a measured medium, so that an indirectly measured value can always be derived from the measured value.

@Measuring transducer 2" is only schematically represented in FIG. 3. As with the measuring transducers described earlier, it can also be embodied, for example, as a single rod, measuring chain having a single housing, in which are formed the measuring half cell as well as the reference half cell. Since the measuring half cell has a solid potential sensing element, the housing of the measuring half cell does not have to be optimized for a sufficient inner electrolyte volume to be available. The measuring half cell can be embodied, thus, very compactly, especially in the form of a layered system connected to the housing of the reference half cell.

Another example of a measuring transducer for determining the pH value of a measured medium is a potentiometric measuring transducer comprising a measuring half cell, which comprises a metal oxide electrode, for example an antimony electrode. Such an antimony electrode, also referred to as antimony oxide electrode, comprises antimony metal covered by a thin layer of antimony (III) oxide $Sb_2O_3$. The reference half cell of the measuring transducer can be embodied in the same way as the reference half cell 300 of the measuring transducers 2 and 2' shown in FIG. 1 and FIG. 2. Alternative materials which can be used for a pH sensitive metal oxide electrode in a measuring half cell of a potentiometric measuring transducer are mercury/mercury oxide, iridium oxide, platinum oxide, tin oxide or titanium dioxide. The general setup of such a measuring transducer corresponds to the measuring transducer as shown schematically in FIG. 3. Instead of the solid potential sensing element 110' a corresponding metal oxide electrode can be used, which is separated by the polymer membrane 10 selectively conducting $H^+$ and/or $OH^-$ ions from the measured medium. In this way, the selectivity of the metal oxide electrode is increased, since any other reducing or oxidizing species present in the measured medium are prevented from influencing the potential of the metal oxide electrode by the membrane.

Figure 4:
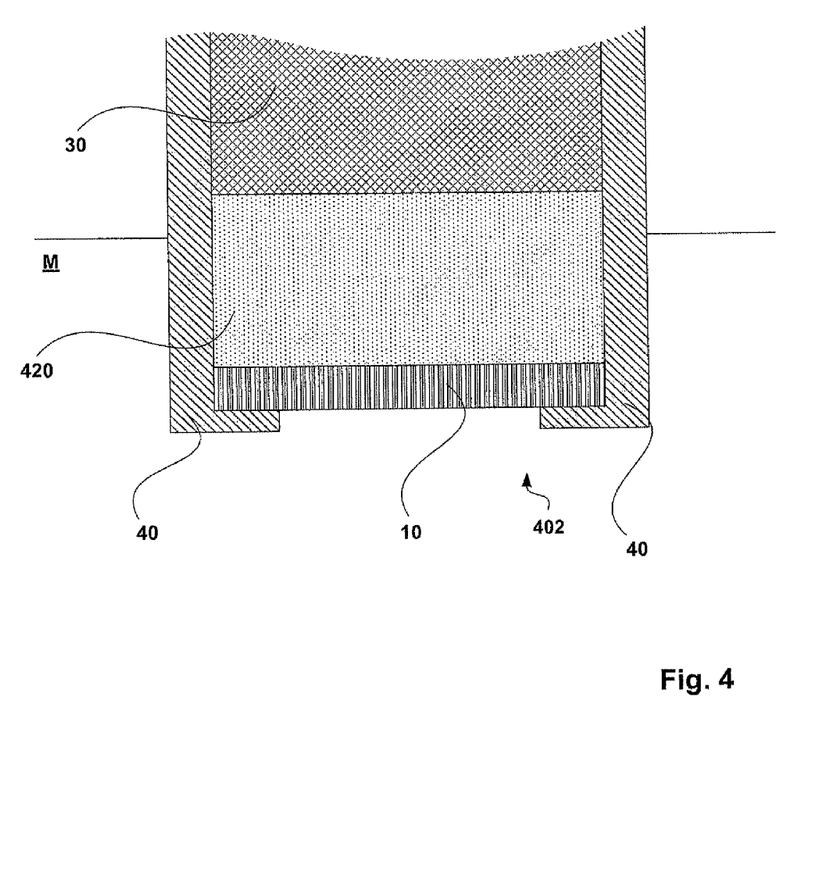
FIG. 4 is an optical measuring transducer for determining a measured variable representing an $H^+$ or $OH^-$ content in a measured medium.

FIG. 4 shows a front end of an optical measuring transducer 402 for immersion in a measured medium M for determining a measured variable thereof, for example, a pH value of measured medium M, representing an $H^+$ content of measured medium M. Optical measuring transducer 402 uses a selectively proton conducting, polymer membrane 10 and includes a housing 40, in which a hydrous sensor matrix 420, for example, a hydrogel, is contained with a pH indicator immobilized in the sensor matrix. The housing is sealed on its end intended for immersion in a measured medium M by a polymer membrane 10, which, thus, spatially separates sensor matrix 420 from the measured medium M. Within housing 40 on the side of sensor matrix 420 facing away from polymer membrane 10, one or more light conductors 30 adjoin on sensor matrix 420 and serve to shine light for exciting a fluorescence of the indicator immobilized in the sensor matrix or to shine light for performing an absorption measurement on the indicator immobilized in the sensor matrix, or to conduct fluorescent light or light, whose intensity is changed by absorption by the indicator, reflected in the area of the sensor matrix, to a detector element (not shown). The detector element can comprise, for example, one or more photodiodes. The detector element can be arranged within housing 40 or be separated from the optical measuring transducer and be connected to the sensor matrix by means of the light conductor. The detector element produces a measurement signal, which is dependent on the intensity of the fluorescent light or the intensity of the light weakened through absorption, received by the detector element; the measurement signal can be further processed by an additional measurement circuit, in given cases, present and output to a superordinated unit, for example, a measurement transmitter, a bus coupler, a programmable logic controller, a personal computer or a process control station.

Polymer membrane 10 can be a polymer membrane comprising an $H^+$ conducting polymer. While without polymer membrane 10 a number of other substances, especially ions, present in the measured medium, in given cases, can diffuse into sensor matrix 420 and lead to undesired side reactions with the indicator immobilized in sensor matrix 420, which can lead to corruption of the measurement results, it is assured by polymer membrane 10, acting as a proton conducting, separating diaphragm, that only $H^+$ ions from the measured medium reach the sensor matrix. This leads to a considerable increase in the selectivity of optical measuring transducer 402.

An $OH^-$ ion conducting, polymer membrane can likewise be used as an isolating diaphragm in an optical pH or pOH measuring transducer.

Figure 5:
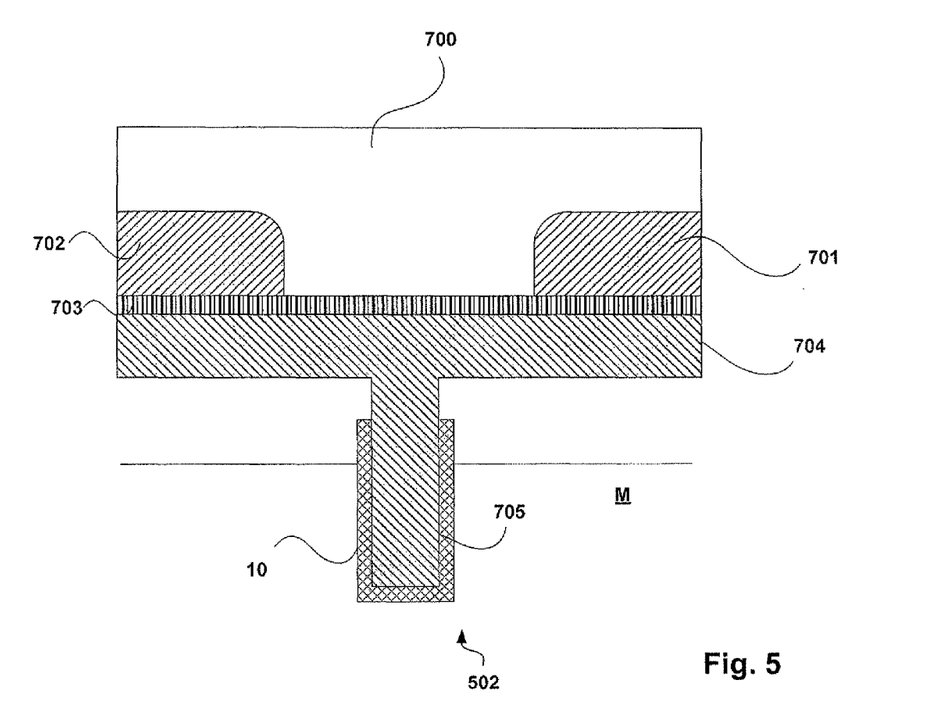
FIG. 5 is a FET measuring transducer for determining a measured variable representing an $H^+$ or $OH^-$ content in a measured medium.

FIG. 5 shows a schematic, sectional illustration of a measuring transducer 502 having a sensitive element based on a field effect transistor (FET), especially a field effect transistor having a metal oxide semiconductor structure, also referred to as MOSFET. Measuring transducer (502) comprises a chip integrated on a silicon substrate 700. A silicon oxide layer 703 on silicon substrate 700 forms the gate oxide of the measuring transducer and stabilizes the field effect induced due to a potential lying on metal layer 704 adjoining silicon oxide layer 703. The field effect enables a channel current between source 701 and drain 702, which are formed, respectively, by p doped or n doped regions of the silicon substrate. Metal layer 704 is conductively connected to a metal wire 705, for example, a platinum wire, which is coated with a proton conducting polymer in a section intended for contact with measured medium M. This polymer coating forms a selectively proton conducting, polymer membrane 10, which separates wire 705 spatially from the measured medium. Due to the selective proton conduction of polymer membrane 10, a potential essentially only dependent on the pH value of measured medium M occurs on wire 705 and correspondingly on metal coating 704 of the gate of the MOSFET measuring transducer. The channel current of the field effect transistor, thus, forms a measurement signal of measuring transducer 502 shown in FIG. 5 representing the pH value of measured medium M. An analogous construction can correspondingly be realized using a selectively hydroxide ion conducting, polymer membrane 20 instead of the proton conducting, polymer membrane.

The invention claimed is:

1. A measuring transducer, which is embodied to produce and output a measurement signal dependent on the content of $H^+$ and/or $OH^-$ ions present in a measured medium, comprising:
    at least one polymer membrane selectively conducting $H^+$ and/or $OH^-$ ions, in a region provided for contact with the measured medium, wherein:
    conduction of $H^+$ and/or $OH^-$ ions occurs intrinsically by means of structural diffusion by transfer of $H^+$ ions and/or $OH^-$ ions between neighboring functional groups of said polymer membrane;
    said polymer membrane comprises an $OH^-$ ion conducting polymer.

2. The measuring transducer as claimed in claim 1, wherein:
    said polymer membrane comprises an $H^+$ ion conducting polymer.

3. The measuring transducer as claimed in claim 1, wherein:
    conduction of $H^+$ and/or $OH^-$ ions occurs intrinsically by means of a Grotthuss-type mechanism.

4. The measuring transducer as claimed in claim 1, wherein:
    said polymer membrane comprises an anhydrous polymeric proton conductor, which has a basic polymer structure, especially a polysiloxane, polystyrene or polythiophene, basic polymer structure, to which groups serving as proton solvent are bonded via side chains, especially flexible side chains.

5. The measuring transducer as claimed in claim 4, wherein:

the groups serving as proton solvent comprise at least one aromatic, heterocyclic compound, especially comprising at least one of the heterocyclic compounds from the group formed by imidazole, benzimidazole or pyrazole.

6. The measuring transducer as claimed in claim 4, wherein:
additionally, acid groups are bonded via side chains, especially flexible side chains, to the basic polymer structure, especially acid groups comprising sulfonic acid, and/or carboxyl, groups.

7. A measuring transducer, which is embodied to produce and output a measurement signal dependent on the content of $H^+$ and/or $OH^-$ ions present in a measured medium, comprising:
at least one polymer membrane selectively conducting $H^+$ and/or $OH^-$ ions, in a region provided for contact with the measured medium, wherein:
conduction of $H^+$ and/or $OH^-$ ions occurs intrinsically by means of structural diffusion by transfer of $H^+$ ions and/or $OH^-$ ions between neighboring functional groups of said polymer membrane;
said polymer membrane spatially separates a sensitive element of the measuring transducer from the measured medium.

8. The measuring transducer as claimed in claim 7, wherein:
said sensitive element comprises a field effect transistor assembly.

9. The measuring transducer as claimed in claim 7, wherein:
the measuring transducer is an optical measuring transducer; and
said sensitive element comprises a sensor matrix, especially a polymer membrane or a porous solid body, having a pH or pOH sensitive indicator immobilized by the sensor matrix.

10. The measuring transducer as claimed in claim 7, wherein:
the measuring transducer comprising a metal oxide electrode, in particular an antimony electrode; and
said polymer membrane selectively conducting $H^+$ and/or $OH^-$ ions spatially separates the metal oxide electrode from the measured medium.

11. A measuring transducer, which is embodied to produce and output a measurement signal dependent on the content of $H^+$ and/or $OH^-$ ions present in a measured medium, comprising:
at least one polymer membrane selectively conducting $H^+$ and/or $OH^-$ ions, in a region provided for contact with the measured medium, wherein:
conduction of $H^+$ and/or $OH^-$ ions occurs intrinsically by means of structural diffusion by transfer of $H^+$ ions and/or $OH^-$ ions between neighboring functional groups of said polymer membrane; and
the measuring transducer is embodied as a potentiometric pH probe.

12. The measuring transducer as claimed in claim 11, further comprising:
a measuring half cell, said measuring half cell comprising a housing, which encloses a measuring half cell space, said housing being sealed by said polymer membrane selectively conducting $H^+$ and/or $OH^-$ ions in a region of the measuring transducer provided for contacting the measured medium.

13. A measuring transducer, which is embodied to produce and output a measurement signal dependent on the content of H+ and/or $OH^-$ ions present in a measured medium, comprising:
at least one polymer membrane selectively conducting $H^+$ and/or $OH^-$ ions, in a region provided for contact with the measured medium; wherein:
said polymer membrane spatially separates a sensitive element of the measuring transducer from the measured medium;
the measuring transducer is an optical measuring transducer; and
said sensitive element comprises a sensor matrix, comprising a pH or pOH sensitive indicator immobilized by the sensor matrix.

14. The measuring transducer as claimed in claim 13, wherein:
the sensor matrix is a polymer membrane or a porous solid body.

* * * * *